United States Patent [19]

Baker

[11] Patent Number: 4,509,212
[45] Date of Patent: Apr. 2, 1985

[54] MULTIPLE-USER OPTICAL ANALYZER SYSTEM USING OPTICAL NETWORK FOR DATA TRANSMISSION AND CONTROL

[75] Inventor: Richard Baker, Medfield, Mass.

[73] Assignee: Corning Glass Works, Corning, N.Y.

[21] Appl. No.: 473,771

[22] Filed: Mar. 10, 1983

[51] Int. Cl.³ ............................................. H04B 9/00
[52] U.S. Cl. .................................. 455/612; 250/227; 350/96.16; 356/409; 356/436; 455/607
[58] Field of Search ............... 455/607, 612, 600, 606, 455/610, 608; 370/1, 3, 4; 350/96.16; 250/227, 231 R; 356/409, 436

[56] References Cited

U.S. PATENT DOCUMENTS 4,223,216  9/1980  Quick et al. ........................ 250/227

FOREIGN PATENT DOCUMENTS 55-109043  8/1980  Japan ................................ 455/608

OTHER PUBLICATIONS

Yajima et al.—Optically Linked Laboratory.

*Primary Examiner*—Joseph A. Orsino, Jr.
*Attorney, Agent, or Firm*—K. van der Steere

[57] ABSTRACT

A multiple-user optical analyzer system is disclosed which comprises a centralized optical analyzer and multiple remote user stations, the user stations being connected to the central analyzer by low-loss optical transmission lines which are shared for the transmission of sample color information and optical communication and control signals for system operation.

3 Claims, 3 Drawing Figures

MULTIPLE-USER OPTICAL ANALYZER SYSTEM USING OPTICAL NETWORK FOR DATA TRANSMISSION AND CONTROL

BACKGROUND OF THE INVENTION

The present invention relates to apparatus for analyzing samples by means of spectrophotometric techniques, and particularly to a multi-user system for obtaining such analyses at remote user locations throughout a hospital, clinic or the like using a simple optical communications/control network.

Devices utilizing a light-transmitting fiber optic link to transmit optical information from a light source to a sample and from a sample to colorimetric analyzer are known. U.S. Pat. No. 4,123,172 describes a comparison-type colorimeter wherein flexible light pipes are used to transmit source light to a sample, and reflected light from the sample to a colorimeter for analysis. G.B. No. 1,525,989 discloses a similar system for use in the colorimetric analysis of solutions, wherein source light is transmitted across a gap between a pair of light transmitting rods in the solution and then transmitted via a fiber optic link to a colorimeter for analysis.

Systems such as shown in the prior art are designed for use at a single fixed location. The multi-element fiber optic linkages used to connect source, sample and analyzer elements in those systems could not practically be expanded for use in a multistation, remote-access environment. Further, no features which would permit control of the system by remote users are provided.

SUMMARY OF THE INVENTION

It is therefore a principal object of the present invention to provide a multiple user system for optical analysis wherein low-loss optical communications linkages are used for the transmission of optical data, system control and communications information within the system.

It is a further object of the invention to provide a multiple user system for the colorimetric or optical absorption analysis of samples at remote sample input stations wherein the stations are connected to a central optical analyzer by low-loss optical transmission lines which are shared for optical data, control and communications signals.

Other objects and advantages of the invention will become apparent from the following description.

The central element of the multiple-user optical analyzer system of the invention is an optical analyzer capable of receiving optical data signals transmitted over optical fibers from two or more remote sample input stations. By optical data signals is meant colored light, the color of which is characteristic of selective absorption or reflectance of a light source by a sample. In response to those data signals, the analyzer generates electrical output signals carrying information about the intensity of selected light frequencies present in the optical data signals which are received.

The system further comprises multiple (two or more) remote sample input stations, each station being adapted to generate optical data signals carrying color information about a sample input by a system user at that station. The stations are connected to the optical analyzer by low-loss optical fibers which transmit the data signals to the analyzer with minimum attenuation.

User terminal means are also provided at each input station for purposes of system control. Each terminal is spliced into the optical fiber connecting the input station with the analyzer, and is adapted to generate or receive optical communications or control signals for transmission over the fiber.

An analyzer controller for the system is also provided, connected to the analyzer and to the optical fiber or fibers from all of the user terminals. This controller supervises the operation of the analyzer during the transmission of optical data signals from a station. The controller also responds to optical communications or control signals received over the fiber from the terminals, and can generate optical control or communications signals for transmission back to the terminals over the same fiber.

Such a system offers significant advantages over previous systems for providing colorimetric or other optical analytical capabilities to multiple users. Only one spectrophotometer unit at the central analyzer is required to service a large network of sample input stations, and placement of the input stations can provide convenient bedside or office access to the system. The system can utilize an existing optical waveguide communications network, or a single-fiber optical transmission network can be installed which the system can share with other optical communications data transmission equipment.

BRIEF DESCRIPTION OF THE DRAWING

The invention may be further understood by reference to the drawing, wherein.

DETAILED DESCRIPTION

Figure 1:
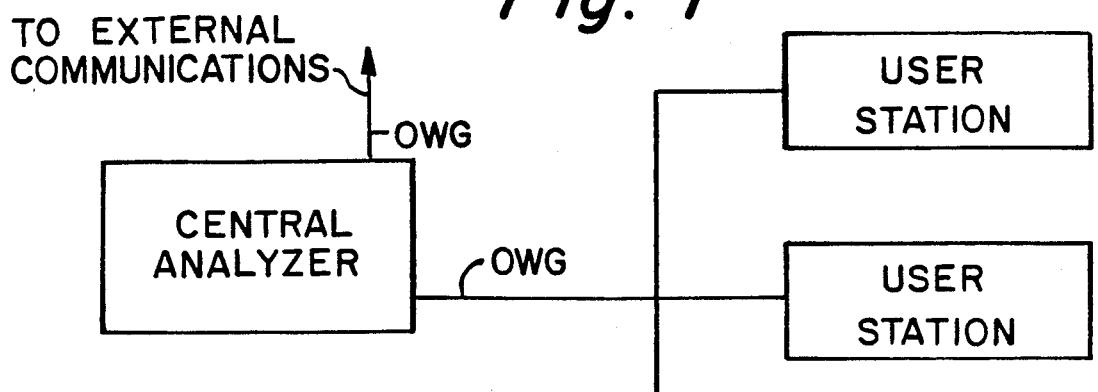
FIG. 1 schematically illustrates a layout for a multi-user optical analyzer system provided according to the invention.

The central optical analyzer of the system of the invention typically includes a spectrophotometer which, by means of a suitable combination of filters and photocells, provides an electrical output signal proportional to the intensity of selected optical wavelengths or ranges of optical wavelengths present in an optical data signal received at the analyzer over the optical fiber transmission line. The optical data signal can comprises visible and/or near infrared light, i.e., light within the wavelength range of about 0.4–2.0 microns. As with conventional systems, the signal will carry information about the spectral absorption or reflectance of a sample input at a user station.

The analyzer may include circuitry to process electrical signals generated by activated photocells therein in order to generate absolute or relative intensity values for selected wavelengths of light present in the optical data signals received. Preferably, however, such processing will be carried out by the analyzer controller as hereinafter more fully described.

The remote sample input stations to be used in the system typically comprise a light source for sample illumination and condensing means for gathering light reflected by or transmitted through a sample, and for launching it into the optical fiber. A sample holder is provided for positioning the sample at a fixed location with reference to the source and condenser.

A typical sample is a fluid sample with respect to which the absorption of selected wavelengths in the source spectrum will have to be measured for colorimetric analysis. In that case, the sample can be introduced in a cuvette which can be positioned in the sample holder between the light source and the input end of the optical fiber, so that the signal carried by the fiber will contain information about the absorption characteristics of the sample.

It is desirable to position the illumination source within the sample input station, rather than transporting source light from a separate location via light pipes as in the prior art, in order to maximize the intensity of the optical signal to be transmitted over the optical fiber transmission line. Commercially available optical fibers, particularly of the kind suitable for the transmission of digital control and communications information, have relatively small core dimensions (e.g., typically on the order of 100 microns or less) and thus are not well suited for the transmission of large amounts of optical power.

The optical fibers utilized for the interconnection of the analyzer and remote sample input stations will normally be low-loss, multimode optical waveguide fibers such as those presently used for optical communications. Preferably, they will be pure glass fibers having outer dimensions not exceeding about 200 microns, core diameters in the range of about 40-100 microns, and optical attenuations as low as a few db/km in the near-infrared portion of the optical spectrum. Most preferably the fibers will be composed of fused silica or doped fused silica and will have attenuations not exceeding about 15 db/km over the wavelength range 0.5-1.3 microns. The use of graded-index fiber having high information-carrying bandwidth, while not required for the analyzer-sample station link, may be desirable to facilitate the transfer of control signals and processed data between the analyzer controller and the user terminal, which will also use the link.

The user terminal located at each remote sample input station will include keyboard or other input means for requesting access to the system or commanding the system into a data input mode. Where the system is designed for multi-testing capability, i.e., running any one of a series of colorimetric tests on clinical samples, the input means will be used to request configuration of the system for the particular test desired.

The user terminal will also include display means by which information concerning the status of the system, systems requests for input, and spectrophotometer report data may be displayed. This could be a cathode ray tube display or, preferably, a low-cost liquid crystal or light emitting diode display.

The analyzer controller preferably includes a control computer which will respond to requests or commands entered at a user terminal, provide status or test information at the terminal, and supervise the operation of the analyzer where such is required. In a system designed for multi-testing capability, the analyzer controller will store information for each test procedure, including information relating to necessary user prompts, appropriate analyzer operation for the test requested, and data processing, storage, or reporting procedures to be followed for the test.

The control of analyzer operation may include control of analyzer calibration, filter selection, and photodiode selection. User prompts may include requests issued by the analyzer controller for the sequential input of blank, standard and unknown samples at the sample input station. Error message prompts may be displayed where optical data signals are not being received as expected by the computer. The control computer will normally be provided with processing software for each test which will generate the necessary user prompts, process signals from the analyzer, store or transmit processed absorption or reflectance data, and report test results to the user in any desired form, e.g., as concentration levels of a particular constituent in solution.

In typical operation, a user at a sample input station will request access to the analyzer system via the terminal keyboard and, in a multi-testing system, will provide information to the controller concerning the analysis which is to be run. The controller will then prompt the user for sample inputs, including any required standard sample inputs, as necessary to perform the analysis required. The controller will supervise analyzer operation, including appropriate sensor and/or filter selection as required, and will receive and process the output of the analyzer utilizing software appropriate for the test being conducted. The controller will then store and/or send the results to the terminal display as requested by the user.

Referring to the Drawing, FIG. 1 illustrates a schematic layout for a typical multi-user spectrophotometer system incorporating a centralized integrated analyzer/controller and three remote user stations comprising integrated sample input terminal modules. The system communications links consist of low-loss glass optical waveguides (OWG).

Figure 2:
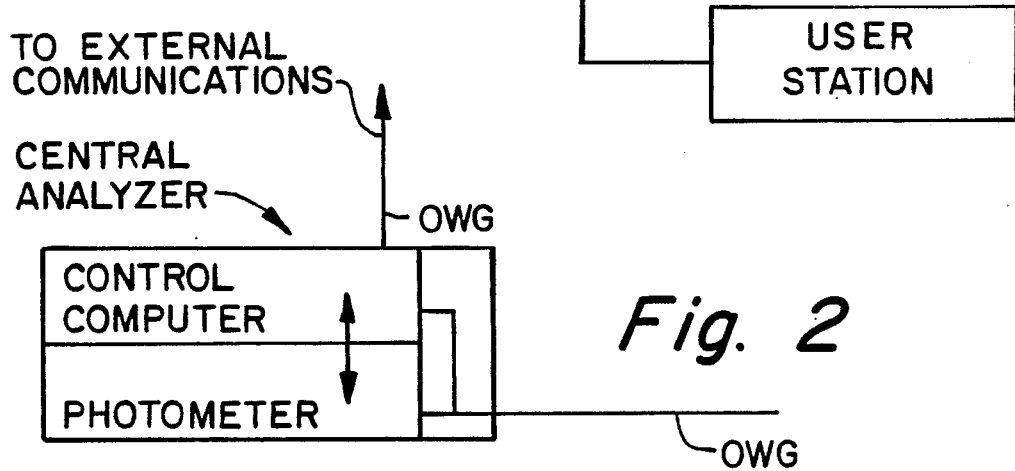
FIG. 2 schematically illustrates a central optical analyzer useful in such a system, and FIG. 3 schematically illustrates a user terminal/sample input station useful in such a system.

A schematic illustration of the centralized analyzer/controller is shown in FIG. 2. The analyzer is a spectrophotometer and the controller is a digital computer which can accept and transmit analog or digital signals over electrical connections to the spectrophotometer (double arrow) for data acquisition and control. Both the spectrophotometer and the computer are connected to the optical waveguide link, the computer being connected for communication with the user terminals and the analyzer for data input from the sample input stations.

Figure 3:
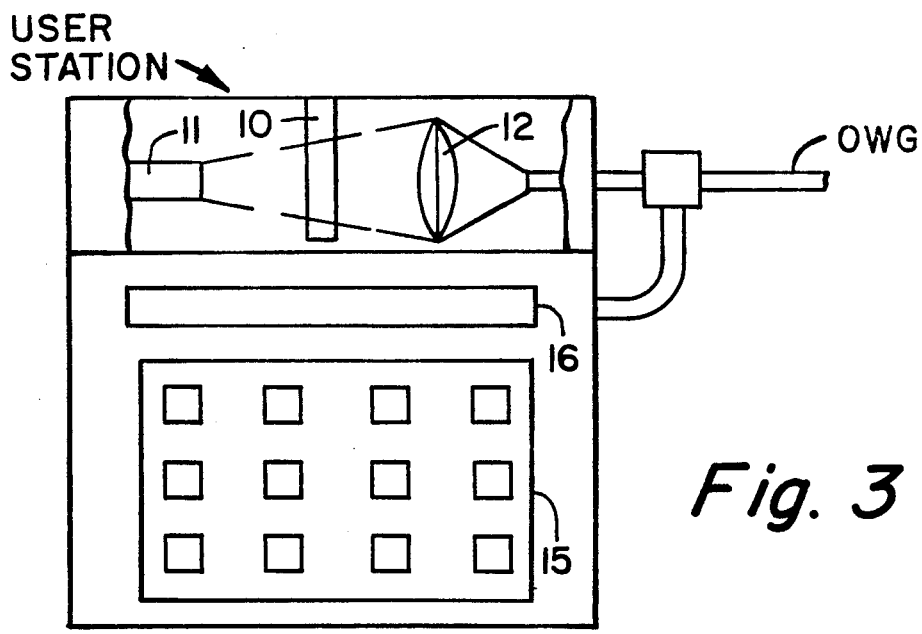

FIG. 3 schematically illustrates a functional design for a user station comprising a sample input station or module and a user terminal. The sample input module includes a sample holder 10 for insertion e.g., of a cuvette, a light source 11, and condensing means 12 for collecting and focusing light traversing the sample holder into the waveguide link (OWG). The terminal includes a keyboard 15 and a display screen 16 for transmitting and receiving information over the optical waveguide link directly connected thereto.

An important advantage of the use of a centralized controller in this system is the possibility of making test results and data available to interested third parties. With proper identification, system subscribers could access the system from any remote location via a standard computer terminal using a commercial telecommunications network, and could receive processed data and report information by digital transmission from the controller. Thus test results could be made available without direct access to a user station. Third party access is schematically shown in FIG. 1 and 2 of the drawing by an OWG link to external communications, typically a commercial telephone computer network.

I claim:

1. A multiple-user analyzer system comprising:

a centralized optical analyzer for receiving optical data signals from a remote sample input station and generating at least one electrical signal of an intensity proportional to the intensity of at least one selected frequency of the optical data signal;

multiple remote sample input stations for generating optical data signals containing color information about a sample inserted at the station by a system user, each station being connected to the analyzer by a low-loss optical fiber capable of transmitting optical data to the analyzer with low attenuation;

user terminal means connected to the optical fiber at each remote input station for generating or receiving optical communication or control signals transmitted over the optical fiber during system operation; and analyzer controller means connected to the optical fiber and to the optical analyzer for controlling the operation of the analyzer during the receipt of optical data signals from a remote input station, and for generating or receiving optical communication or control signals carried over the fiber between the controller means and the user terminal means.

2. In spectrophotometer apparatus wherein a light signal containing color information imparted by reflection from or transmission through a colored sample is transmitted for color analysis from the sample to an optical analyzer spaced at a location remote from the sample by transparent fiber optical conduction means, the improvement wherein:

the fiber optical conduction means consists of a low-loss optical fiber transmission line;

the light signal originates from a sample input station which comprises a sample holder for positioning a sample for transmission or reflection of light into said low-loss optical fiber transmission line, and a light source in proximity with the sample holder for generating the light for reflectance or transmission;

user terminal means are provided proximate to the sample input station for generating optical communication or control signals to be transmitted to the optical analyzer; and the sample input station and user terminal means are both connected to the optical analyzer by said low-loss optical fiber transmission line.

3. Apparatus in accordance with claim 2 which further comprises analyzer controller means connected to the optical fiber transmission line and to the optical analyzer for controlling the operation of the analyzer during the receipt of light signals for color analysis, and for generating or receiving optical communication or control signals carried over the optical fiber transmission line between the analyzer controller means and the user terminal means.

* * * * *